(12) United States Patent
Yang

(10) Patent No.: US 7,936,457 B2
(45) Date of Patent: May 3, 2011

(54) SYSTEM AND METHOD FOR DETECTING AND ANALYZING PARTICLES UTILIZING ONLINE LIGHT SCATTERING AND IMAGING TECHNIQUES

(75) Inventor: Jie Yang, S. Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 282 days.

(21) Appl. No.: 12/245,274

(22) Filed: Oct. 3, 2008

(65) Prior Publication Data
US 2009/0091757 A1  Apr. 9, 2009

Related U.S. Application Data

(60) Provisional application No. 60/977,168, filed on Oct. 3, 2007.

(30) Foreign Application Priority Data

Mar. 19, 2008 (CA) ....................................... 2630374

(51) Int. Cl.
*G01N 21/00* (2006.01)

(52) U.S. Cl. ........................................ 356/338; 356/337
(58) Field of Classification Search .......... 356/335–344, 356/73, 244, 246, 440, 39, 409–411; 250/573–576
See application file for complete search history.

(56) References Cited

U.S. PATENT DOCUMENTS

| | | | |
|---|---|---|---|
| 4,616,927 | A | 10/1986 | Phillips et al. |
| 4,854,705 | A | 8/1989 | Bachalo |
| 5,404,217 | A | 4/1995 | Janik et al. |
| 5,530,540 | A | 6/1996 | Wyatt et al. |

*Primary Examiner* — Gregory J Toatley
*Assistant Examiner* — Tri T Ton
(74) *Attorney, Agent, or Firm* — Downs Rachlin Martin PLLC

(57) ABSTRACT

A chromatographic system that includes a light source and an imaging and analysis system for detecting particle size and analyzing other characteristics of particles in the effluent of a filtration column while filtration is ongoing. The effluent is directed into a guiding tube having a flow axis. Coherent light from the light source is shone into the guiding tube along the flow axis, thereby illuminating particles in the effluent within the guiding tube. An imaging device is used to capture images of the portion of the light scattered by the particles. The image signals are analyzed and used to provide information regarding particle size and other characteristics of the particles in the effluent scattering the light.

27 Claims, 11 Drawing Sheets

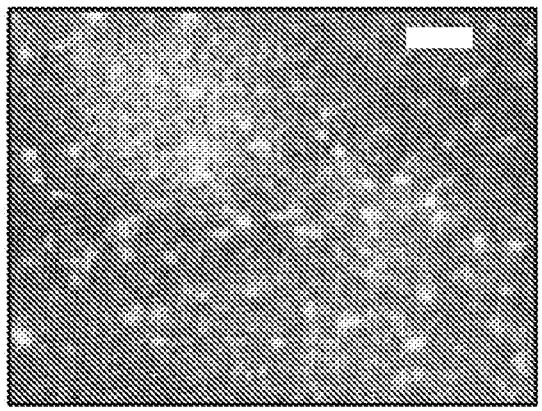 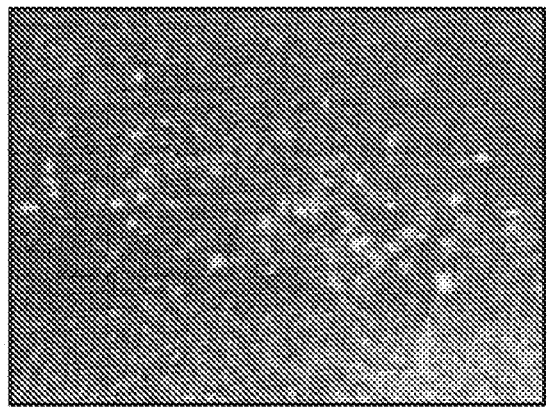
FIG. 7(a)  FIG. 7(b)
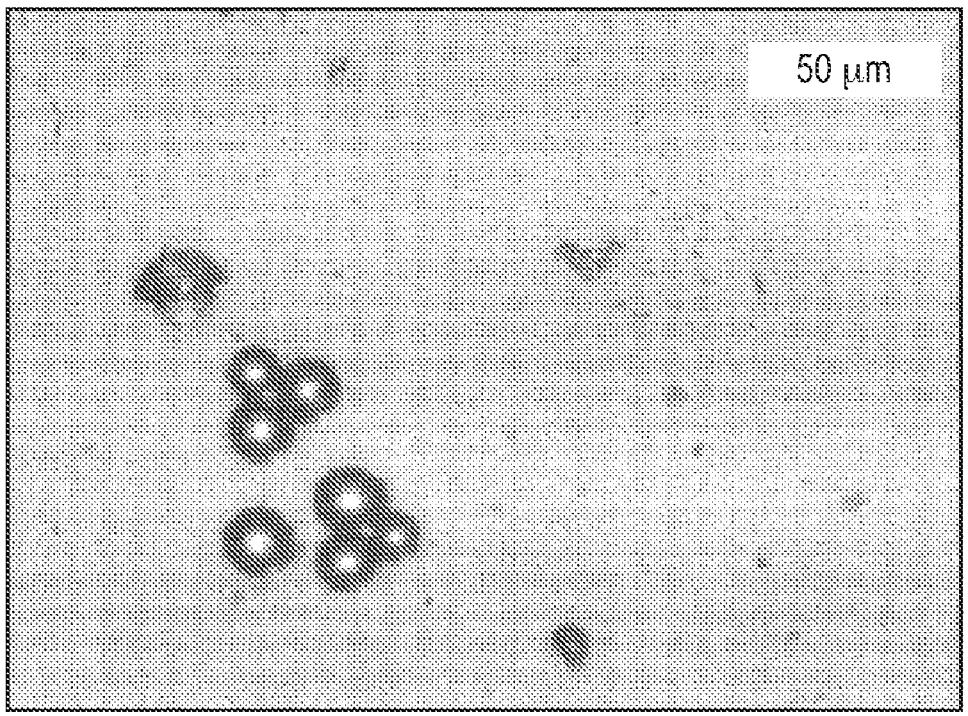
FIG. 8

SYSTEM AND METHOD FOR DETECTING AND ANALYZING PARTICLES UTILIZING ONLINE LIGHT SCATTERING AND IMAGING TECHNIQUES

RELATED APPLICATION DATA

This application claims the benefit of priority of U.S. Provisional Patent Application Ser. No. 60/977,168, filed Oct. 3, 2007, and titled "System and Method for Performing Liquid Chromatography, Gel Filtration, and/or Particle Purification," which is incorporated by reference herein in its entirety. This application also claims the benefit of priority of Canadian Patent Application No. 2,630,374, filed Mar. 19, 2008, and titled "System and Method for Detecting and Analyzing Particles Utilizing Online Light Scattering and Imaging Techniques," which is also incorporated by reference herein in its entirety.

FIELD OF THE INVENTION

The present invention generally relates to the field of particle detection and identification in chromatographic systems. In particular, the present invention is directed to a system and method for detecting and analyzing particles utilizing online light scattering and imaging techniques.

BACKGROUND

Gel filtration (size exclusion chromatography) and high-performance liquid chromatography (HPLC) have been widely used in separation and purification of soluble proteins. Both methods employ filtration columns, but the column packing materials are different. Most common packing materials are polymers for gel filtration and porous silicon particles for HPLC. Polymers are often preferred for biological applications for the convenience of not requiring any additional chemical modification. It is well-known that in filtrations processes, microscopic pores of the packing material effectively elongate flow paths for soluble proteins and that the net path increase for a protein depends on its molecular weight. Thus, differing proteins elute at differing times in a filtration run, allowing identification and purification according to the elution pattern. With HPLC, usually silicon particles are chemically modified to better facilitate biological applications because the silicon surface is hydrophobic and thus is prone to air bubbling that markedly affects the continuous uniform flow of the transport liquid in filtration runs.

Dynamic light scattering (DLS) is well-known in the context of measuring hydrodynamic sizes, polydispersities and aggregation effects of protein samples. In a conventional DLS setup, a fixed volume of a transport liquid containing the protein samples under investigation is placed in a transparent cell and laser light is shone into the cell. A photodetector is then used to measure the laser light that is scattered from the protein particles suspended in the transport liquid. Fluctuations of the scattering intensity due to the Brownian motion of the particles are recorded and used to determine the sizes, polydispersities and aggregation effects of protein samples according to well-known techniques.

SUMMARY OF THE DISCLOSURE

One implementation of the present invention is a system for performing at least one of gel filtration, liquid chromatography and particle purification. The system includes: a liquid system containing a packing material and receiving a mixture containing particles during use, the fluid system defining a flow path for facilitating smooth flow of the mixture; a light source configured and located to illuminate a portion of the flow path with coherent light in a direction along the flow path so as to cause light scattering by ones of the particles in the mixture; and an optical sensor for detecting the light scattering.

Another implementation of the present invention is a liquid chromatographic system. The system includes: a filtration column containing a packing material; a fluid delivery system for providing a transport liquid to the filtration column under pressure; a guiding tube located downstream from the filtration column, the guiding tube having a flow axis; a light source for providing coherent light beam; a light transmission unit fluidly coupled between the filtration column and the guiding tube, the light transmission unit for transmitting the coherent light beam along the flow axis of the guiding tube so that when a mixture of particles and the transport liquid is flowing through the guiding tube the particles cause scattering of the coherent light beam; and an imaging system for obtaining image signals of the scattering.

Still another implementation of the present invention is a method of performing at least one of particle detection, particle identification and particle characterization. The method includes: flowing a liquid mixture containing particles through a packing material so as to produce an effluent from the packing material; flowing the effluent through a guiding tube; illuminating at least a portion of the effluent in the guiding tube with light; sensing a portion of the light scattered by ones of the particles in the guiding tube so as to provide light-scattering data; and collecting the light-scattering data over a period of time.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7a is an image of pure transport liquid (2× phosphor-buffered saline (PBS)) obtained using the 90 mW green laser (the scale of the bar is 0.1 mm);

FIG. 7b is an image of pure transport liquid (2× PBS) obtained using the 0.5 mW red laser;

FIG. 8 is an image of Sephacryl® S-200 HR polymeric packing particles after letting a suspension of these particles dry on a glass slide;

DETAILED DESCRIPTION

Figure 1:
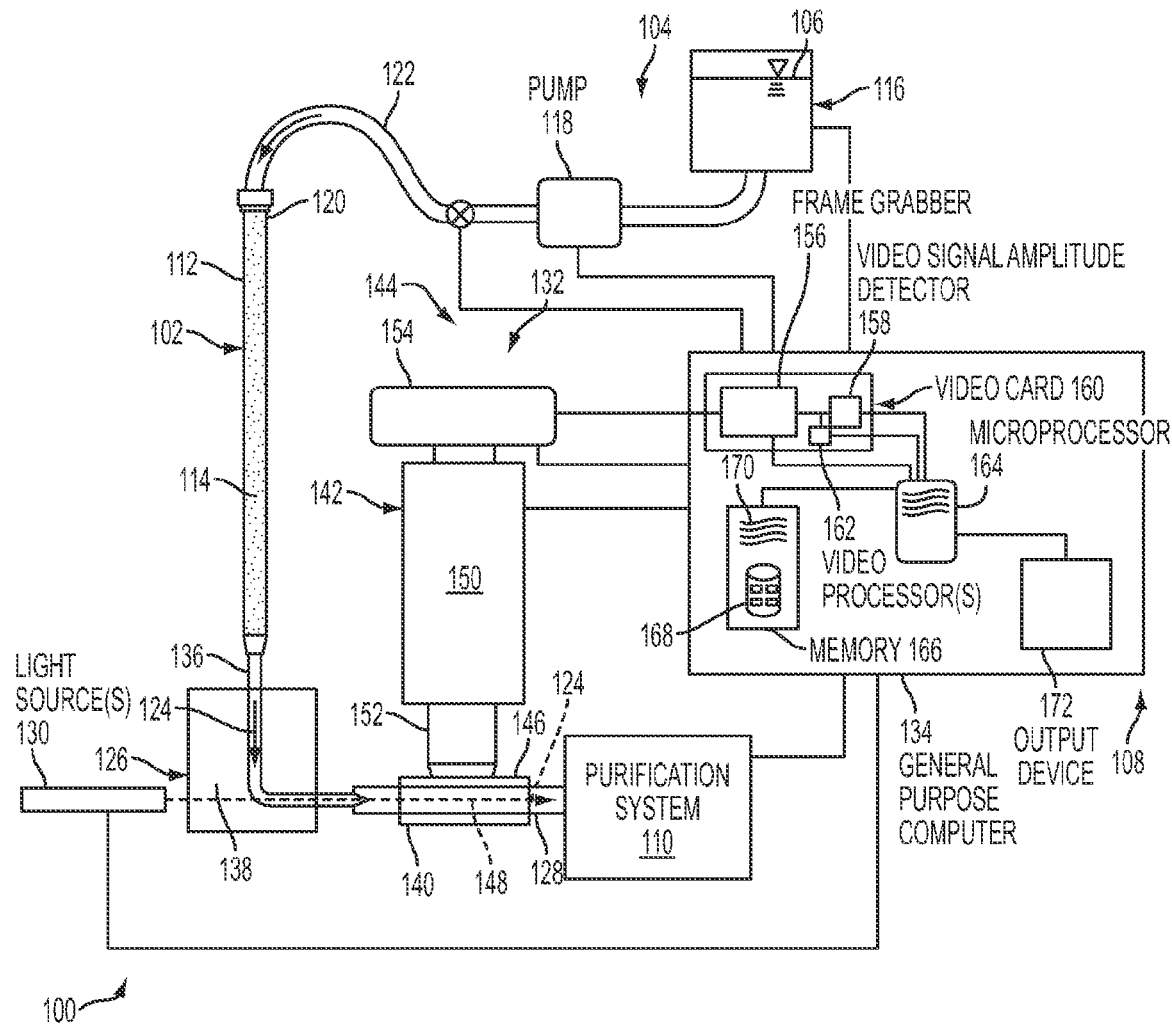
FIG. 1 is a partial elevational view/partial high-level schematic view of a liquid chromatographic (LC) system.

Referring now to the drawings, FIG. 1 illustrates an example of a liquid chromatographic (LC) system 100 made in accordance with concepts of the present invention. At a general level, LC system 100 includes a filtration column 102, a liquid delivery system 104 for delivering a transport liquid 106 to the filtration column and an online light-scattering particle detection/analysis system 108 for detecting particles in the effluent of the filtration column, and their characteristics, and optionally analyzing these characteristics. In the context of the present disclosure and the claims appended hereto, the term "online" means that particle detection/analysis system 108 operates in real-time as the effluent of filtration column 102 is flowing through the detection/analysis system. As described below in detail, particle detection/analysis system 108 provides LC system 100 with a powerful online tool useful for a number of purposes, such as particle identification and characterization and chemical detection and classification, among others.

It is noted that while an online particle identification/analysis system made in accordance with concepts disclosed herein may be used in a variety of analytical and practical applications, such as gel filtration, size exclusion chromatography (SEC), high-performance liquid chromatography (HPLC) and particle separation, among others, LC system 100 of the present embodiment is directed to purification, i.e., separation of differing particles from one another. Consequently, LC system 100 includes a purification system 110. In one specific example, LC system 100, including purification system 110, is configured for purifying soluble proteins. Those skilled in the art will understand techniques that can be implemented in purification system 110, such that further details are not necessary for those skilled in the art to understand how to implement LC system 100. Particle detection/analysis system 108 is describe in detail below. However, prior to describing particle detection/analysis system 108, other components of LC system 100 are first described immediately below because they provide context for the detection/analysis system.

Filtration column 102 includes a tube 112 filled with a packing material 114 suitable for the application at hand. In the present example in which LC system 100 is configured for purification of soluble proteins, tube 112 is a capillary tube having an inside diameter of 1.8 mm and packing material 114 is Sephacryl® S-200 HR polymeric particles (Sephacryl is a registered trademark of GE Healthcare Bio-Sciences AB, Sweden (formerly registered to Pharmacia)). This setup was used for experimental purification of samples containing various combinations of bovine albumin (66 kilo Daltons (kD)), lysozyme (14 kD) and ovalbumin (44 kD). Those skilled in the art will readily appreciate that in other embodiments, tube 112 may have any other size for the type of filtration being conducted and packing material 114 may be any other packing material suitable for the filtration being conducted.

It is noted that while tube 112 is shown as being straight and having a circular transverse cross-sectional shape, in other embodiments it may have another longitudinal shape, such as zig-zag, spiral, and helical, and may have another cross-sectional shape, for example, square, rectangular, etc. The length of tube 112 may be any length suitable for the intended application. In experiments described below in the Experimental Section, the length of tube 112 was varied among several runs from 40 cm at the short end of the range to 80 cm at the long end. Alternative packing materials suitable for use as packing material 114 are well-known in the art and include polymeric and non-polymeric packing materials. Examples of suitable packing materials include, but are not limited to, polymer beads, porous silicon particles, spherical and non-spherical particles, among others. The type, size, shape, and other characteristics of packing material 112 may be selected in accordance with the particular implementation of LC system 100.

Liquid delivery system 104 may include a reservoir 116 for holding transport liquid 106 for use during the operation of LC system 100 in moving a sample (not shown) of particles to be purified through the LC system. Reservoir 116 will typically be sized to hold enough transport liquid for one or more purification runs as desired. In the present example, LC system 100 is a pressurized system wherein transport liquid 106 is pumped through filtration column 102, particle detection/analysis system 108 and purification system 110. Consequently, in this example liquid delivery system 104 includes a pump 118 to provide the flow of transport liquid 106 through filtration column 102 and particle detection/analysis system 108. (That said, it is noted that LC system 100 can be operated without pump 118, with the flow through the system being osmotic flow.) Suitable pumps that may be used for pump 114 are well-known in the art, as is the knowledge to select a proper size pump for the flow rate(s) that LC system 100 is designed to handle. As an example, in the context of the 1.8 mm inside diameter capillary tube filled with Sephacryl® S-200 HR packing material, flow rates used in two runs were 0.0167 mL/min and 0.0063 mL/min. Of course, in other implementations, the flow rates can be different.

In the embodiment shown, LC system 100 is configured such that prior to each purification cycle a sample (again, not shown) to be purified is added to filtration column 102 at its upstream end 120. To facilitate this, liquid delivery system 104 includes a conduit 122 that is removably engaged with filtration column 102 in a manner that allows the conduit to be readily removed from, and replaced onto, the filtration column before and after the sample is added to the filtration column, respectively.

At a high level, particle detection/analysis system 108 includes a fluid pathway 124 for receiving transport liquid 106 and any sample (not shown) present in the transport liquid to, in this example, purification system 110. Fluid pathway 124 comprises a light transmission unit 126 and a guiding tube 128. Particle detection/analysis system 108 also includes one or more light sources 130, for example one or more lasers, for providing coherent light to fluid pathway 124, an optical/imaging system 132 for detecting light scattered from particles in the transport liquid/sample mixture flowing through guiding tube 128 and a detection/analysis system, here a general purpose computer 134, for analyzing data captured by the optical/imaging system. In the exemplary runs with the soluble proteins mentioned above, three light sources were used at differing times: a 5 mW green pointer laser, a 90 mW green pointer laser and a 5 mW helium neon red laser. Of course, in other embodiments, lasers of other colors and/or other powers may be used to suit a particular setup. In addition, it is noted that more than one light source 130 is desirable particularly when they are arranged to promote interference of the light scattered by the particles in the transport liquid/sample mixture within guiding tube 128.

In this embodiment, light transmission unit 126 includes a multitask tube 136 immersed in a refractive-index compensation medium 138, here oil, for example. As used herein and in the appended claims, the term "multitask tube" means a tube that performs multiple tasks, such as: 1) transmitting illumination light from the one or more light sources 130 into fluid pathway 124, specifically, in a direction along the longitudinal axis of guiding tube 128; 2) providing smooth (laminar), continuous solution flow with very low chance of bubble generation; 3) inhibiting stray light from reaching optical/imaging system 132; 4) retaining coherence of the transmitted light; and 5) directing transmitted illumination light onto the eluted transport liquid/sample mixture stream so that particles in the eluted stream are showered with the illumination light so as to cause light scattering for detection by the optical/imaging system.

Figure 2:
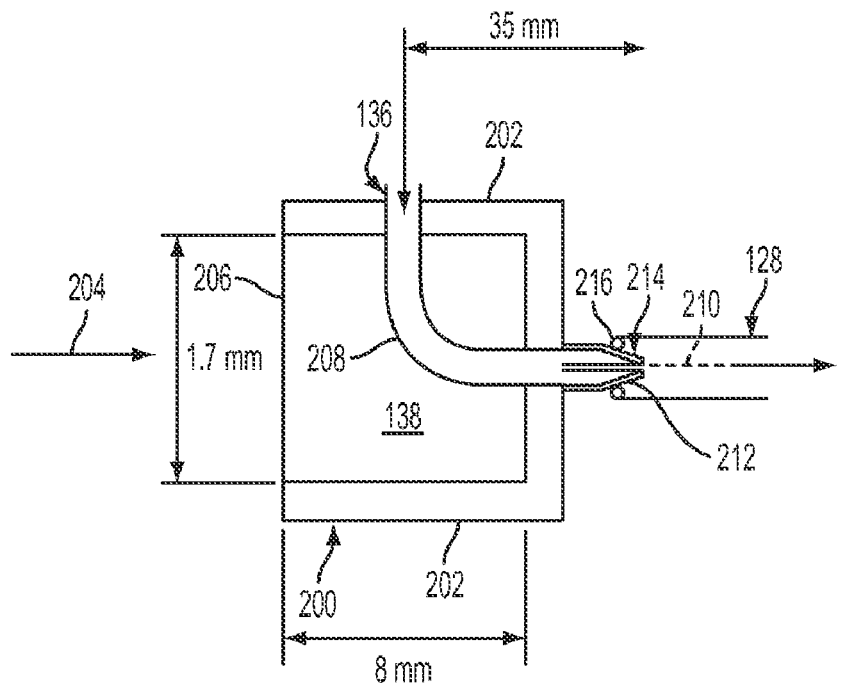
FIG. 2 is an enlarged cross-sectional view of the light transmission unit and a portion of the guiding tube of FIG. 1.

Referring now to FIG. 2, and also to FIG. 1, FIG. 2 illustrates in more detail light transmission unit 126 of FIG. 1. As seen best in FIG. 2, light transmission unit 126 includes an immersion cell 200 having walls 202 that are opaque to the incident light beam 204 from the one or more light sources, and a window 206 for receiving the incident light. Opaque walls 202 inhibit the incident light from reaching optical/imaging system 132 (FIG. 1) and interfering with the light actually scattered from the particles in the transport liquid/sample mixture flowing in guiding tube 128. In this embodiment, multitask tube 136 has a uniform, radiussed bend 208 that counsels the use of a suitable refractive index matching medium 138 within immersion cell 200 to direct incident light beam 204 into guiding tube 128 in a direction along the longitudinal central axis 210 (which is also the flow axis) of the guiding tube. In this example, multitask tube 136 has a light-apertured cone-shape tip 212 that is provided with an opaque coating 214, for example, a black paint, that, like walls 202 of immersion cell 200, inhibit stray light from reaching optical/imaging system 132 (FIG. 1).

In the experimental setup that included the 1.8 mm inside diameter capillary tube for filtration column 102, multitask tube 136 may be made from a similar capillary tube. In this case, the capillary tube is heated and bent into an L-shape. Cone-shaped tip 212 may be formed by heating one end of the capillary tube and pulling that end so as to form a cone shape. A mechanical device and a torch flame may be used for forming the cone-shape in a more controlled manner. During use, incident light beam 204 is transmitted through cone-shaped tip 212 along one leg of L-shaped multitask tube 136.

Still referring to FIGS. 2 and 1, in the embodiment shown there, guiding tube 128 is a thin-walled glass tube that is provided separately from multitask tube 136 and is fluidly sealed to the multitask tube using a soft, rubbery O-ring gasket 216 that provides a leak-tight joint. In other embodiments, other means known in the art may be used to join guiding tube 128 to multitask tube 136. Although FIGS. 1 and 2 illustrate multitask tube 136 and guiding tube 128 as being separate pieces joined using a gasketed joint, in other embodiments the guiding tube may be formed monolithically with the multitask tube. In one example of this monolithic construction, cone tip 212 may be replaced by a suitably-shaped insert that is installed into the monolithic piece. In addition, it is noted that although multitask tube 136 is shown as being L-shaped, it may have another shape. For example, in some embodiments, the multitask tube may be U-shaped.

Figure 3A:
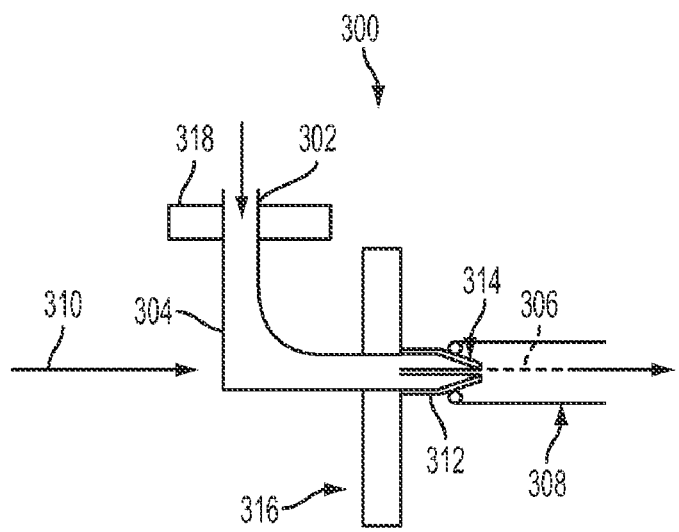
FIG. 3A is a cross-sectional view of an alternative light transmission unit suitable for use in an LC system of the present disclosure.
Figure 3B:
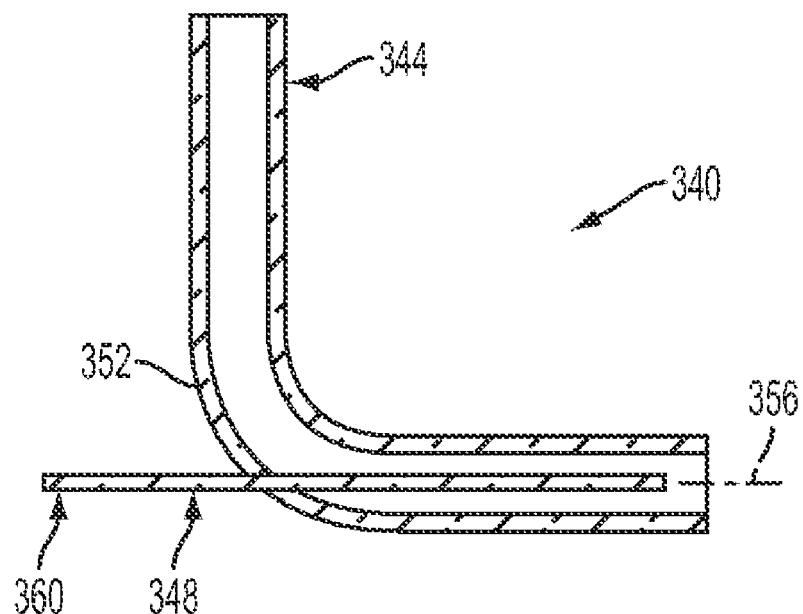
FIG. 3B is a cross-sectional view of another alternative light transmission unit suitable for use in an LC system of the present disclosure.

In this connection, if the guiding tube is monolithically formed with the multitask tube, the multitask tube may have multiple directional transitions. For example, in the context of a U-shaped piece, the guiding portion may be either the "base" portion between the two outstanding legs or, alternatively, one of the legs. The incident light beam, then, may be shone through a corresponding respective one of the transitional bends into the guiding portion, for example, in the manner described above. In yet other embodiments, wherein a light source is incorporated inside the multitask tube along the flow axis thereof, say using an optic fiber, the "multitask tube," which would no longer be required to perform a number of the tasks described above, may even be straight and coaxial with the guiding tube. FIG. 3B illustrates an optic-fiber type light transmission unit 340 that comprises a simple 90°-bend tube 344 having an optic fiber 348 extending through the wall 352 of the tube so as to extend along the flow axis 356 of one leg of the tube. Those skilled in the art will readily appreciate that one end 360 of optic fiber 348 would be optically coupled to one or more suitable coherent light sources (not shown). In alternative embodiments, 90°-bend tube 344 may be replaced by a tube of another shape, such as straight. In a straight-tube embodiment, the optic fiber could be bent as appropriate to make the light exiting the fiber extend along the flow axis of the tube proximate the guiding tube (not shown).

In FIGS. 1 and 2, light transmission unit 126 includes an immersion cell 200 because of the radiussed-bend configuration of multitask tube 136. In other embodiments, immersion cell 200 can be eliminated. One example in which an immersion cell is not needed was mentioned briefly above. This is where the light source is incorporated directly into the multitask tube, for example, using an optic fiber that enters the multitask tube. Another example is shown in FIG. 3A, which shows an alternative light transmission unit 300 in which the multitask tube 302 is L-shaped like multitask tube 136 of FIGS. 1 and 2, but where the directional transition is specially formed to include a flat and smooth surface 304 that is perpendicular to the flow axis 306 of the guiding tube 308. Consequently, an incident light beam 310 can be shone directly on surface in a direction perpendicular thereto to avoid the need for correcting any directional changes in the light beam due to refractive bending of the beam due to oblique incidence angles. Other aspects of multitask tube 302, such as cone-shaped tip 312 and opaque coating 314, may be the same as the corresponding aspects of multitask tube 136 of FIGS. 1 and 2, as may be the means for joining guiding tube 308 to multitask tube 302. Multitask tube 302 may be supported in any suitable manner, such as by a pair of support bars 316, 318 or other support structure. In this example, support bar 316 is opaque (or otherwise made to be opaque) to avoid stray light from reaching optical/imaging system 132.

Referring again to FIG. 1, optical/imaging system 132 includes an optical cell 140, a magnification system 142 and an imaging system 144. Optical cell 140 hosts guiding tube 128 and, in this example, is filled with water (not shown) and covered with a glass cover slip 146 to facilitate the detection of scattered light by magnification system 142 and for imaging in online laser light scattering. Water is used in this example because of its effect on the optics of the system. The eluted particles from filtration column 102 are in a mixture with water when transport liquid 106 is, e.g., a saline solution, and guiding tube 128 is made of thin glass. In this case, the optical properties of the water is essentially the same as the optical properties of the transport liquid. Because of the thin glass of guiding tube 128, light rays through the guiding tube are only altered very slightly. However, if instead guiding tube 128 is in air, the differences of refractive indices of water (transport liquid), glass (the wall of guiding tube) and air will alter greatly the path of light, which may be prone to generating stray light rays that would enter magnification system 142 and negatively impact the performance of optical/imaging system 132. If cover slip 146 is not provided, the upper surface of the water in optical cell 140 would provide an air-water interface. Although under an ideal situation the air-water surface is absolutely flat, the air-water surface is normally prone to air current fluctuations in ambient conditions. In addition, evaporation causes gradual lowering of the interface. These conditions will alter the optical path of the scattered light entering magnification system 142 and will generate noise and/or undesirable artifacts as seen by the magnification system.

Magnification system 142 provides microscopic imaging of a focal plane 148 within guiding tube 128 from which it is desired to capture light-scattering data concerning light from the coherent beam shone into the guiding tube that is scattered by particles in the transport liquid/sample mixture flowing therethrough. In the present embodiment, magnification system 142 includes a conventional microscope 150 having an objective lens 152 positioned immediately adjacent cover slip 146 of optical cell 140. In other embodiments, magnification system 142 may include custom optics or system other than a conventional microscope.

Imaging system 144 of this example includes a charge-coupled device (CCD) imaging device, such as an intensified CCD video camera 154, attached to the head of microscope 150. Video camera 154 is used for capturing images that include scattered light scattered from the particles in the transport liquid/sample mixture flowing through guiding tube 128. These images are then used, for example, using general purpose computer 134 (such as a personal computer or laptop computer), to provide information that can be used to characterize the particles in the transport liquid/sample mixture and/or to separate various size particles from one another, i.e., to purify the particles.

Figure 4:
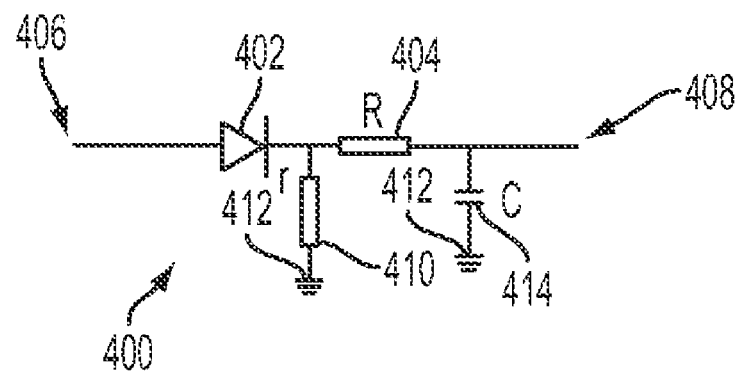
FIG. 4 is a schematic diagram of an exemplary amplitude detector circuit suitable for use in the video signal amplitude detector of LC system of FIG. 1.

To complement video camera 154, imaging system 144 also includes a frame grabber 156 for capturing individual image frames from CCD video camera 154 for the signal processing needed for particle detection and analysis. In the present example, the signal processing is accomplished in part by a video signal amplitude detector 158. FIG. 4 illustrates an example of a video signal amplitude detector circuit 400 suitable for use as video signal amplitude detector 158 of FIG. 1. Video signal amplitude detector circuit 400 includes a diode 402 and a first resistor 404 electrically coupled in series between an input 406 and an output 408, with a second resistor 410 electrically coupled to ground 412 at a node between the diode and the first resistor and a capacitor 414 electrically coupled to ground 412 at a node on the opposite side of the first resistor, as shown.

The amplitude of the video signal is proportional to the average light intensity detected by video camera 154. A summation method may be used to yield the average light intensity. For example, the average light intensity may be obtained by summing over values of all (of a selected number) of pixels (not shown) relative to a common background value and multiplying the summation result by a convenient proportional constant. Image analysis methods, such as methods involving structural pattern classification and recognition, can be implemented to detect matter that interacts with light. Referring again to FIG. 1, such methods may be performed, for example, by general purpose computer 134 or other processing means (either hardware or software or a combination of both) as are known and understood by those skilled in the art. Those skilled in the art will readily appreciate that the various imaging components of optical/imaging system 132 may be configured differently from the configuration shown. For example, frame grabber 156 may be part of video camera 154, rather than part of a video card 160 installed in general purpose computer 134. Likewise, video signal amplitude detector 158, if provided, may be part of video camera 154 rather than being located aboard video card 160. Those skilled in the art will understand the variety of configurations these and other components of optical/imaging system 132 may have.

Still referring to FIG. 1, as described above, information that can be provided/collected includes actual images as captured by video camera 154 and information derived from such images. Regarding the former, in this example general purpose computer 134 includes video card 160 containing frame grabber 156 for capturing images output by the video camera. It is noted that these images may be output not only to a data bus (not shown) or other data path for internal use by computer 134, but they may also be output to, for example, a video monitor for viewing by a user of LC system 100. Regarding the latter, i.e., information derived from the captured images, video card 160 includes video signal amplitude detector 158 as described above. Video card 160 may also include one or more video processors 162 for analyzing and characterizing the images and/or output of amplitude detector 158. Alternatively, if such processing capability is used, it may be provided by one or more microprocessors 164 that form part of computer 134.

The images and/or data derived therefrom is stored in any suitable memory 166 in any manner known in the art, such as in a database 168. Memory 166 may also contain software 170, including appropriate user interface software, for controlling LC system 100 and/or outputting information to a user regarding the state and operation of the system and characterization of the particles in the transport liquid/sample mixture based on the captured images. In this connection, general purpose computer 134 may include one or more output devices 172 and include one or more video monitors and printers. Those skilled in the art will readily understand that computer 134 may, and will typically, contain other components, such as various user-input devices, other software (e.g., operating system) and other internal and external hardware. A description of these other components should not be necessary for those skilled in the art to understand the embodiment shown in FIG. 1. If purification (particle separation) of the transport liquid/sample mixture is a desired outcome, purification system 110 can be controlled by computer 134 (or other controller) to separate particles based on size and perhaps other features as a function of the characterization of the particles determined from the images captured by video camera 154. Computer 134 and purification system 110 may be set up for automatic functioning using suitable control software and hardware. Using the present disclosure as a guide, those skilled in the art would understand how to implement such software and hardware.

Figure 12:
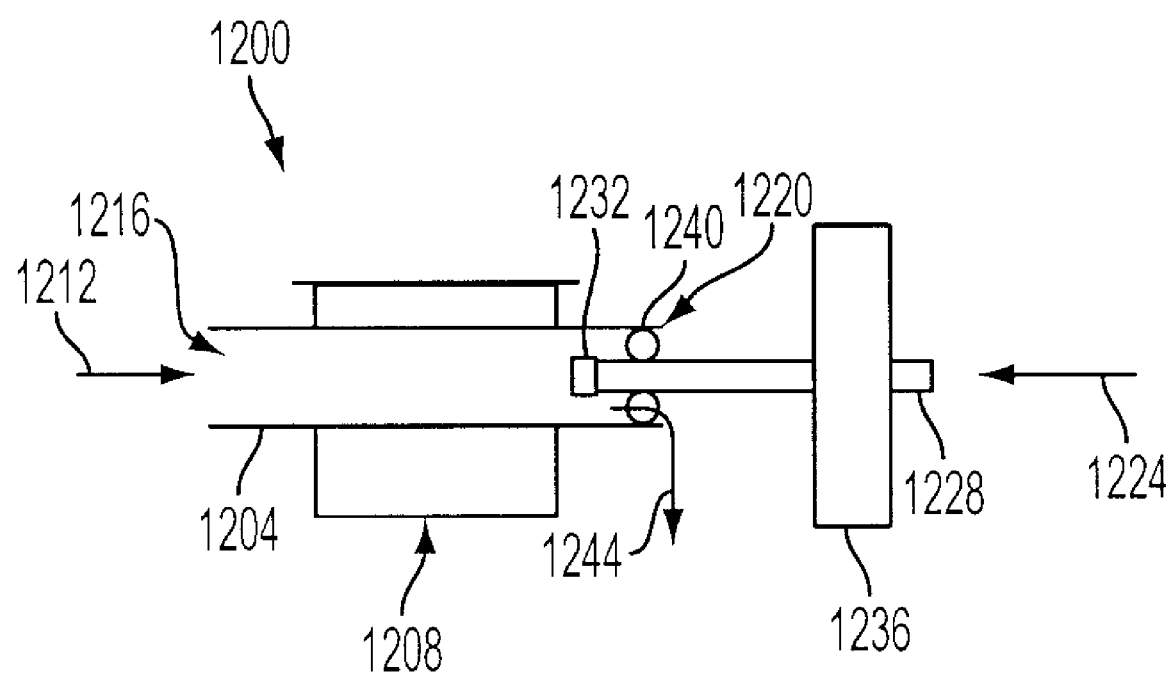
FIG. 12 is a partial elevational cross-sectional view/partial elevational view of an alternative guiding-tube setup suitable for use in an LC system of the present disclosure.

While each of the guiding-tube setups shown in FIGS. 1-3(*b*) includes a multitask tube 136, 304, 344 located upstream of the corresponding guiding tube 128, 308 (where shown), alternative guiding-tube setups do not necessarily require a guiding tube at that location. For example, FIG. 12 illustrates a guiding-tube setup 1200 that does not require a multitask tube upstream of the guiding tube 1204. Referring now to FIG. 12, and occasionally to FIG. 1 for context, guiding tube 1204 extends through an optical cell 1208 in a manner similar to guiding tube 128 extending through optical cell 140 in FIG. 1. This is so for the same reasons discussed above relative to optical cell 140. However, instead of directing light into guiding tube 1204 in the same direction as the flow direction 1212 of the solution eluted from a filtration column, such as column 102 of FIG. 1, as occurs in each of the setups in FIGS. 1-3(*b*), in guiding-tube setup 1200 of FIG. 12, light is directed into guiding tube 1204 in a direction opposite flow direction 1212. By the nature of the arrangement of components of guiding-tube setup 1200, with the solution (not shown) flowing into guiding tube 1204 from its upstream end 1216 (relative to the flow of solution) and with light entering the guiding tube from its downstream end 1220, there is no need for an upstream multitask tube. Indeed, upstream end 1216 of guiding tube 1204 can be fluidly connected to any suitable conduit, such as an elbow, straight run, or directly to the outlet of a filtration column.

In this example, collimated light is shone into guiding tube 1204 in the form of a laser beam 1224, which is directed into the guiding tube via a transmission conduit, such as laser needle 1228. Laser needle 1228 is hollow and so is capped with a transmissive cap 1232 at its end located inside guiding tube 1204 to prevent the solution in the guiding tube to flow into needle. In one example, transmissive cap 1232 is made of glass and is secured to laser needle 1228 with an epoxy adhesive. Transmissive cap 1232 allows direct transmission of laser beam 1224 in a manner that preserves the collimation of the laser light. To assist in stabilizing laser needle 1228 against movement, the laser needle may be firmly supported by a suitable support, here, by an aluminum block 1236 having a suitably sized aperture (not shown) that receives the needle therethrough. In this example, laser needle 1228 is centered within the opening in guiding tube 1204 at downstream end 1220 using a rubber O-ring 1240, which also acts to create a fluid seal between the needle and guiding tube. An effluent capillary draining tube 1244 is provided to allow the solution flowing through guiding tube 1204 to exit the guiding tube to permit the flow of solution through the guiding tube that is needed for an LC system 100 that incorporates guiding-tube setup 1200 to function properly.

It is noted that in some alternative embodiments of guiding tube setups that have a configuration similar to the configuration of guiding-tube setup 1200 of FIG. 12, i.e., setups in which the light is shone in a direction opposite to the direction of solution flow, a multitask tube, such as any one of multitask tubes 136, 304, 344 can be used on the downstream end of the guiding tube. For example, it can be readily envisioned that even laser needle 1228 and capillary draining tube 1244 can be integrated into a multitask tube very similar to multitask tube 344 of FIG. 3(*b*). More particularly, and referring to FIGS. 3(*b*) and 12, optic fiber 348 could be replaced with laser needle 1228, and the rest of tube 344 could function as capillary draining tube 1244. This can be envisioned by rotating light-transmission unit 340 of FIG. 3(*b*) by 180° and attaching the end of tube 344 to downstream end 1220 of guiding tube 1204 in FIG. 12 and making the laser-needle substitution just mentioned. Despite the above-highlighted physical differences between guiding-tube setup 1200 of FIG. 12 and other guiding-tube setups described herein, the basic functioning of setup 1200 is virtually the same as described for other embodiments and examples. Therefore, the details of operation of guiding-tube setup 1200 need not be described here, as it would be duplicative. This is true also for other embodiments made in the spirit of guiding-tube setup 1200.

EXPERIMENTAL SECTION

Materials and Instruments

The following description can be largely related to LC system 100 of FIG. 1, though there were some minor differences between the setup illustrated in FIG. 1 and the setup used in actual experiments. These differences include the fact that the experimental setup did not include central control by a general purpose computer and did not include a purification system, as shown and described relative to FIG. 1. That said, those skilled in the art will recognize the great similarities between the experimental setup described below and LC system 100 of FIG. 1. Indeed, the reader is encouraged to use FIG. 1 as a guide while reading this Experimental Section.

Proteins and fluorescein isothiocyanate isomer I (FITC) were obtained from Sigma-Aldrich (St. Louis, Mo.) as lyophilized powders. Phosphate-buffered saline (PBS) in powder form was obtained from Sigma-Aldrich and dissolved into distilled and deionized water to 0.2× PBS as filtration transport liquid. Sephacryl® S-200 HR (S-200) and blue dextran 2000 (BD2000) polymeric particles were obtained from Pharmacia. Major instruments used in experiments included pointer green lasers of 5 mW and 90 mW, a 5 mW helium neon red laser from Melles Griot, a Nikon Optiphote 2 light microscope, and an intensified CCD camera from Photo Technology International (PTI, Monmouth, N.J.). The laser beam from the red laser is linearly polarized, and that from the green lasers is not. However, power output from the green lasers is not isotropic either. There is an optimal polarization axis corresponding to the maximum laser power output. This optimal axis can be determined by inserting a linear polarizer in the light path of the laser beam and monitoring the output as the polarizer rotates.

Capillary Tip Preparation

A capillary tube was bent to an L shape, and one end of the tube was pulled to a cone. FIG. 2 is a rough sketch of the light transmission unit used in the experimental setup, with key dimensions given but not drawn in proportion. The multitask, or "L tube," was sealed in a cell filled with optical immersion oil. The glass window allowed beaming the laser at the capillary tube. The side surface of the cone was coated with black paint so that the laser light was transmitted from the tip only. A glass guiding tube was coupled to the tip to confine eluted solution, also useful for future purification applications. The capillary L tube had a rather large diameter (5.5 mm) and a bore diameter of approximately 0.5 mm. The cone tip had a diameter of about 1 mm. Such a large tip enhanced light transmission efficiency and allowed a small degree of freedom to slightly vary the incident angle without any loss of the transmitted intensity and total power.

Signal Detection and Data Recording

The objective lens of the light microscope was focused inside the guiding tube at the level of the transmitted laser beam so that the CCD camera collected scattered lights by objects around the focal plane. Thus, the camera was a sensor of orthogonal scattering, in contrast to small-angle scattering in other studies. The video output from the CCD camera was fed to a monitor and a filter box in parallel. The output from the filter box was a dc voltage proportional to the integrated average video amplitude, allowing monitoring of scattering intensity continuously in filtration runs. The conversion factor relating this voltage to the light intensity was not determined, but all data collected were of the same factor.

Packing of the Capillary Column

The capillary column was packed with S-200 particles. They were much smaller than the diameter of the column (1.8 mm), so the packing was done by top loading. Some long columns were made of a zigzag tube to reduce the overall end-to-end length for easy handling and to accommodate realistic space in experimental setup. The column loading time was significantly shortened with the help of a variable flow minipump (from VWR) to drive a faster flow rate. The same pump was also used to drive transport liquid flow in filtration runs.

Flow Rate

The flow rate in milliliters/minute was measured by two methods. The conventional method was to collect the solution at the elution end of the column over a long time to yield the volume flow rate. The imaging capability of the new system allowed direct measurement of the linear flow rate in millimeters/minute and to convert to the volume flow rate by multiplying the cross-sectional area of the guiding tube. The diameter of the guiding tube of 1.18±0.05 mm was measured by a micrometer under a stereomicroscope. In a calibration run, the two methods gave slightly different volume flow rates, 0.0167 mL/min with the conventional method and 0.0177 mL/min with the imaging method. In light of the convenience of direct measurement of the linear flow rate from digitized video images, the latter method was adopted to determine the flow rate.

FITC Labeling

Light-scattering intensity from proteins with fluorescence labeling was stronger. Thus, smaller protein concentration could be used for proteins with fluorescence tags. For labeling, the protein concentration was 10 mg/mL. FITC was dissolved into either dimethyl sulfoxide (DMSO) or ethanol before use at a concentration of 4 mg/mL. A drop of less than 1 μL of FITC solution was applied to the protein solution of about 0.5 mL and followed by thorough mixing. After incubation for 1 hour, the protein solution was transferred to a 10 kD microcon concentrator (Millipore) and centrifuged. Most free FITC molecules were driven out of the concentrator's reservoir and into the centrifuge tube. Afterward, fresh solution was added, and the procedure was repeated. This procedure was repeated several times until the permeated solution was clear. Then, 0.4 mL of PBS was added to the reservoir of about 0.1 mL, and the solution with labeled proteins was collected for later use.

According to classical electrodynamics the quasi-elastic scattering (Rayleigh scattering) intensity is mainly due to dipole radiation, and thus if the incident light is linearly polarized the orthogonal scattering intensity depends on the orientation of the polarization. With the vertical optical axis of the objective lens in the experimental setup, the scattering intensity should be at the maximum for a horizontal polarization, and that was indeed the case with the red laser. As expected, the integrated average intensity was minimal, at a level barely detectable, when the polarization axis of the red laser was vertical. For the green lasers, the optimal polarization axis was oriented horizontal in elution runs, but overall the orientation of the optimal axis did not alter very much the scattering intensity.

Pressurized Capillary Gel Filtration with Regulated Flow Rates

Figure 5A:
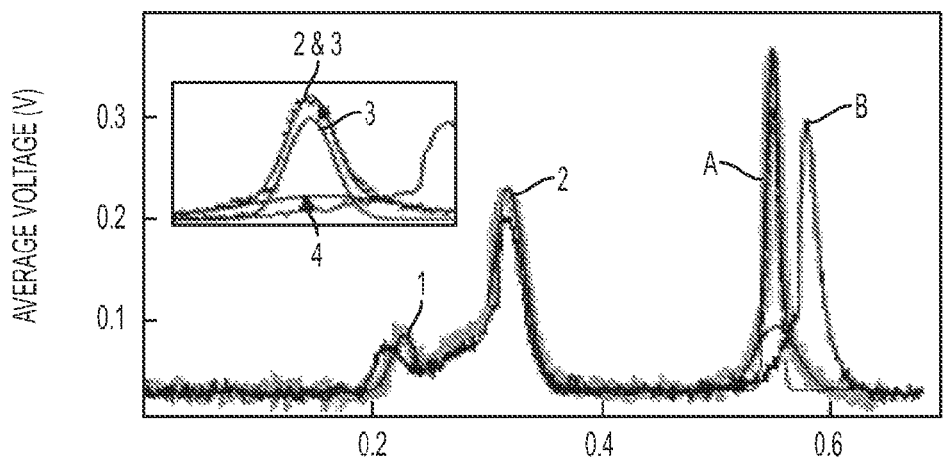
FIG. 5a is a graph of average voltage versus time showing elution profiles for a sample containing 4 µL of bovine albumin (BSA) at 22 mg/mL and lysozyme (LZ) at 89 mg/mL obtained using a 40 cm long filtration column and a 90 mW green laser (the time axis for curve B was arbitrarily shifted to let the MSA peaks of the two curves coincide with one another and the corresponding respective smooth lines are Gaussian fitting curves)
Figure 5B:
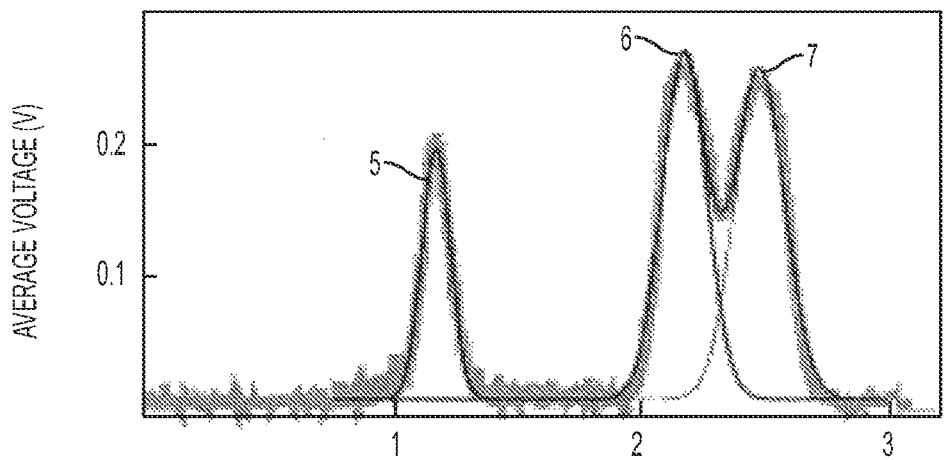
FIG. 5b is a graph of average voltage versus time showing elution profiles for a sample containing 2 µL of fluorescein-isothiocyanate-isomer-I-labeled (FITC-labeled) BSA and ovalbumin of about 5 mg/mL and blue dextran 2000 (BD2000) of about 4 mg/mL obtained using an 80 cm long filtration column and a 5 mW green laser (the corresponding respective smooth lines are Gaussian fitting curves)
Figure 5C:
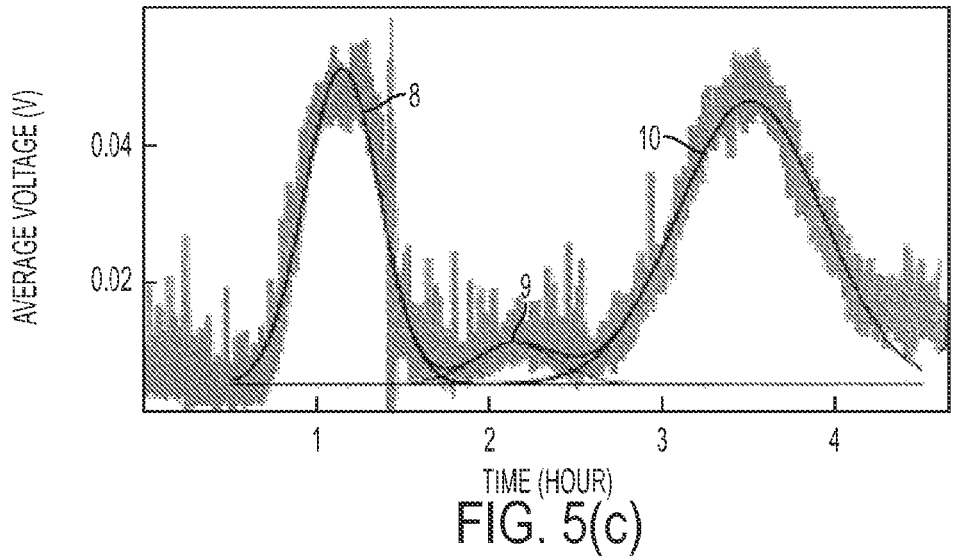
FIG. 5c is a graph of average voltage versus time showing elution profiles for a sample containing 2 μL of BD2000 at 26 mg/mL and FITC-labeled BSA at 10 mg/mL obtained using a 70 cm long filtration column and a 5 mW green laser (the corresponding respective smooth lines are Gaussian fitting curves)

FIGS. 5a-c show elution curves with the vertical axis being the voltage reading proportional to the integrated average scattering intensity. The curve in FIG. 5a was from a sample containing bovine albumin (BSA) (66 kD) and lysozyme (LZ) (14 kD), that in FIG. 5b was from a sample containing BD2000, BSA, and ovalbumin (44 kD), and that in FIG. 5c was from a sample containing just BD2000 and BSA. For the elution curves in FIG. 5a, the flow rate for curve A was 0.030 mL/min (linear speed 0.46 mm/s in the guiding tube) and that for curve B was 0.028 mL/min (linear speed 0.43 mm/s). The filtration runs were done in just about 35 min. The first maximum was due to aggregates of much larger effective masses. The BSA peak was readily differentiated from the LZ peak because of the large difference in their molecular weights. For the sample containing BD2000, BSA, and ovalbumin (FIG. 5b), a slower flow rate of 0.0063 mL/min (linear speed of 0.096 mm/s) was adapted for a satisfactory separation of BSA and ovalbumin with the total elution time of about 3 hours. In this case the first peak included contributions from BD2000 and aggregates, eluting first through the void volume without being affected by pores of the column medium. The flow rate due to osmotic flow alone was much slower as can be seen in FIG. 5c with an extremely long total elution time. The total running time was well over 7 hours. However, the flow rate was not measured in this case because the run did not employ the guiding tube. The reason was that the guiding tube was susceptible to bubble formation and over such a long period there was seldom a case without any bubble generated. With the guiding tube, any bubble that emerged from the capillary tip was trapped against the tip, and that completely disrupted the optical pathway, resulting in extremely bright background. Instead, the tip was directly submerged in a fluid cell that usually allowed the bubble to float away from the tip to clear from the optical path. Note that FIG. 5c only shows elution profiles around the two peaks, missing most parts of the flat background, corresponding to the period when solutes migrated in the column. In this case the transport liquid reservoir was about 1.5 m above the level of the capillary cone tip.

In order to understand the elution process, elution curves in FIG. 2 (except curve B in part a) were fitted to the Gaussian function for correspondingly numbered peaks with the fitting parameters given in the Table immediately below.

TABLE 1

| | Fitting Parameters | | | |
|---|---|---|---|---|
| peaks | width σ (h) | centers c (h) | proportional constants (V) | bases (V) |
| 1 | 0.011 | 0.224 | 0.00158 | 0.0266 |
| 2 | 0.0154 | 0.317 | 0.00296 | 0.0296 |
| 3 | 0.00501 | 0.549 | 0.00356 | 0.0271 |
| 4 | 0.0209 | 0.551 | 0.00309 | 0.0271 |
| 5 | 0.0568 | 1.15 | 0.0267 | 0.0103 |
| 6 | 0.0889 | 2.16 | 0.0575 | 0.0103 |
| 7 | 0.0981 | 2.46 | 0.0608 | 0.0103 |
| 8 | 0.215 | 1.15 | 0.0252 | 0.00428 |
| 9 | 0.244 | 2.17 | 0.00376 | 0.00428 |
| 10 | 0.420 | 3.56 | 0.044 | 0.00428 |

The Gaussian function is of the form $$Gfit(t) = \frac{A}{\sigma\sqrt{2\pi}} \exp\left(-\frac{(t-c)^2}{2\sigma^2}\right) + B \quad (1)$$

where A is a proportional constant, B is the baseline level (very close to zero), t is time, c is the center of the peak, and σ is the width of the peak. The center position depends on the choice of the starting time so that its absolute value is not important. The relative positions of centers for elution curves provide a measure of the resolution of the elution pattern. The width of the peak measures the broadening effect of eluted proteins in the filtration process. Elution peaks in FIGS. 5*a-c* are numbered as shown, and fitting parameters for the corresponding curves are presented in the Table. Consistent with units used in FIGS. 5*a-c*, peak centers and widths are in hours and proportional constants and baseline values are in volts. Overall, for all elution curves, the width becomes wider for later peaks, consistent with the diffusion-caused band broadening of mobile proteins.

Of all elution peaks, the LZ peak stands out for its irregularity, requiring a combination of two Gaussian curves for the best fit. These two fitting functions are of essentially the same center position but drastically different widths. The inset in FIG. 5*a* serves to bring out the feature of the LZ peak with corresponding fitting curves in line plots, where the original data are shown in a scatter plot. The shoulder between the first peak and the BSA peak is likely the result of BSA dimers. Dimers of BSA were also responsible for a small bump in part c (curve 9) of FIG. 5*c*. There were also runs without enough BSA dimers to give rise to the characteristic bump or shoulder, as the case in FIG. 5*b*.

The prominent feature of the LZ peak shows a clear involvement of two types of scattering processes where the one with a wider width (curve 4) is consistent with the elution pattern because the later eluted group is expected to have a wider width. The fitting curve 3 is of a much narrower width that indicates a different scattering mechanism. This phenomenon is examined from several different aspects in this study to be described below, showing that this irregular scattering is actually due to constructive interference.

For the two curves in FIG. 5*a*, the net amount of BSA loaded was 88 μg according to the numbers in the caption, larger than the 40-50 μg used in a report elsewhere. However, the magnitude of the peak seems to suggest that reducing the load amount by half should not be a problem for detection, so in that sense the newly developed instrumentation is on track to have at least a similar detection sensitivity. With the use of the concentration and the amount of samples loaded at the top of the column, the volume flow rate, and the diameter of the guiding tube, it is possible to estimate the sample concentration at the detection site. For the BSA peak, when a crude approximation assuming a rectangular distribution with the width that of the Gaussian distribution is used, the concentration at the detection site was about 3 mg/mL.

With conventional gel filtration, columns are usually of large diameters, easier to maintain constant flow rate over a long period of time, but the spread of solutes is also large as they move through the column. The capillary columns used in this study did suffer a steady decrease of the flow rate under the same pumping power. For the pair of curves shown in FIG. 5*a*, curve B was obtained by a run right after the one that yielded curve A. The flow rate was apparently slowed for the later run from the flow rate measurement. The peak positions relative to those of curve A also indicated a slower flow rate. The net reduction of the flow rate is actually very small, and thus for a column of a larger diameter this effect can be reduced to a negligible level to maintain approximately constant flow over a long time. However, the similarity in general features of the two curves in FIG. 5*a* is remarkable. Moreover, the much smaller spread of proteins in the mobile phase overwhelms the shortcoming of having to maintain an exactly constant flow rate.

Figure 6A:
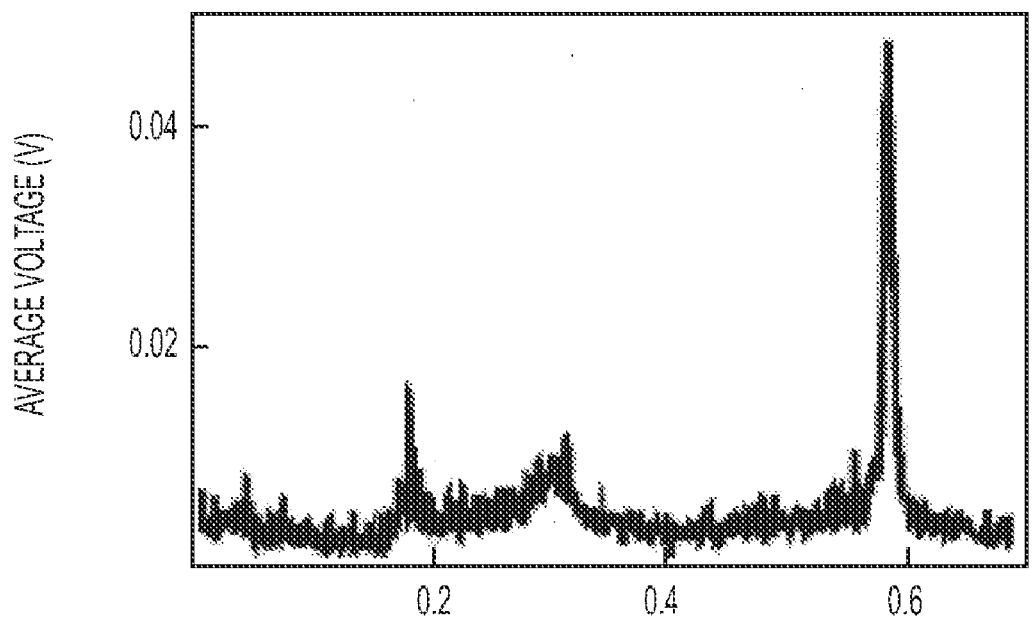
FIG. 6a is a graph of average voltage versus time showing an elution profile for a sample prepared in the same batch as the sample for FIG. 5a obtained using a 40 cm long filtration column using a 5 mW red laser.

The red laser could also result in detectable scattering intensities as shown by a typical example in FIG. 6*a*. The elution curve bares the similar feature as that by the green laser but has much smaller overall amplitudes. The amplitude of the BSA peak is about 0.01 V, and that of the LZ peak is about 0.05 V, giving a ratio of the two amplitudes of about 5. The similar ratio yielded from FIG. 5*a* is much smaller. Thus the irregular scattering is more pronounced in this case.

Figure 6B:
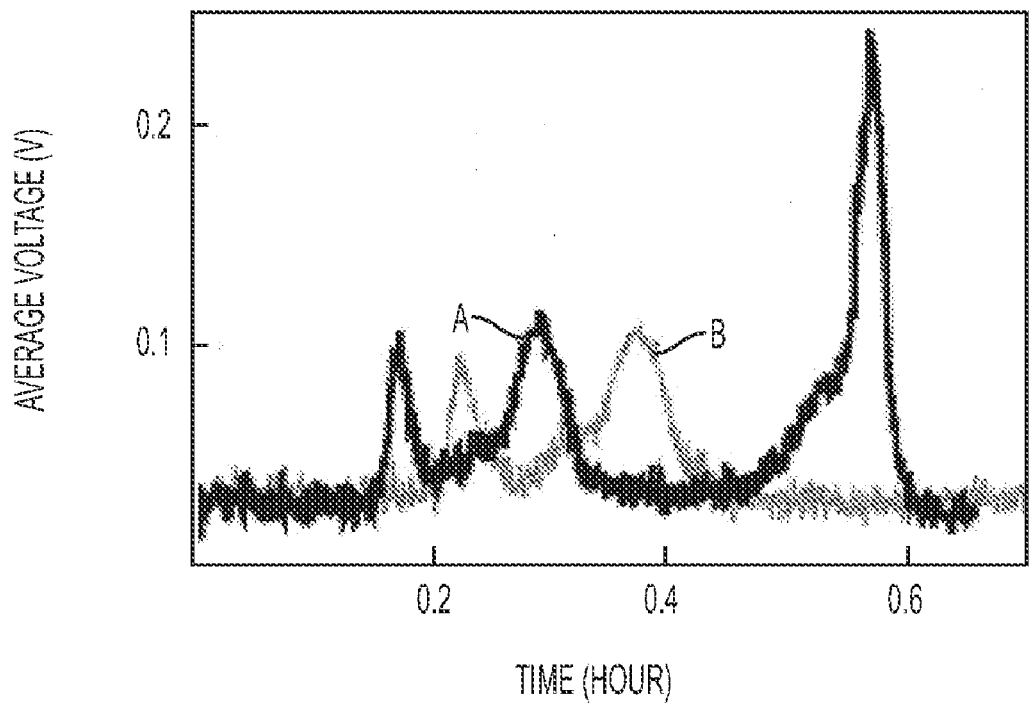
FIG. 6b is a graph of average voltage versus time showing elution profiles for two samples prepared in the same batch as the sample for FIG. 5a obtained using a 40 cm long filtration column using the 90 mW green laser, wherein curve B without LZ scattering was obtained using a very slightly different light incidence angle.

Most surprisingly, with just very slight variation of the incident angle by about 2°, the LZ scattering peak could change from very high in some runs to extremely low in other runs. FIG. 6*b* shows two elution curves by the green laser with a change of the incident angle by 2°. Apparently, the total power and the intensity of the incident laser were almost identical because of the similarity in amplitudes and features of the initial two peaks of both elution curves. Yet, the LZ peak was completely missing in elution curve B. Especially, all samples in FIGS. 6(*a*) and (*b*) and in FIG. 5*a* were prepared from the same batch. This phenomenon suggests that the scattering by LZ is by no means the simple Rayleigh scattering but rather some kind of cooperative and coherent scattering.

Because of the coupling of the incident light through the capillary tube, the meaning of incident angle is not geometrically well-defined regarding the transmitted light from the cone tip, in sharp contrast to the case of reflection and refraction in a homogeneous medium with planar boundaries. In the experiment, as the incident angle varied by about 2°, on the monitor the transmitted beam line was seen to displace from the upper half to the lower half of the screen. According to the calibration, such a displacement was of a range of about 0.2-0.3 mm.

Microscopic Structures of Eluting Materials and Solutions

Imaging of scattering objects in mobile phase serves to better understand microscopic details of how light interacts with matters involved in the filtration process. It is a surprise to find large amount of "particles" (FIGS. 7*a-b*) just by driving pure solutions through gel filtration columns. The more powerful green laser (90 mW) resulted in images of more scattering centers and a brighter background, as seen in FIG. 7*a*. Typical images by the red laser shown in FIG. 7*b* had a darker background and fewer particles. However, in both cases the pure solution was identical. Thus, the lack of "particles" by the red laser was an artifact because of the lower power (or frequency) of the light source.

A note of caution is that not all particles in the image were at the level of the focal plane, so for those particles off the focal plane, the spot size was not an actual measure of the particle size. Moreover, by the nature of scattering, even on the focal plane the size of a bright spot could be much larger than the actual size of the particle. For example, in single-molecule imaging experiments the light emitted from a single fluorophore was detected where the spot size was of the order of the wavelength of the fluorescence light, much larger than the actual size of the single fluorophore. Thus, images like the two shown in FIGS. 7a-b indeed unequivocally reveal the existence of a large amount of scattering centers. These centers must be some kind of particles or aggregates in solution. However, the actual size of them cannot be reliably measured from optical images alone in this case.

The presence of a large amount of scattering centers naturally causes a rather large background scattering. The key for higher sensitivity detection is to enhance the signal-to-noise ratio. However, simply increasing the laser intensity by using higher power lasers is not helpful, because the intrinsically large background scattering also proportionally increases if the laser power increases.

In order to probe the origin of these large particles, optical images of column packing materials were obtained by drying a drop of S-200 polymer suspension on a glass slide and imaging with a light microscope. FIG. 8 shows a typical image of dried S-200 particles. There are round particles with diameters in the range of 10-20 μm and irregular debris of a wide range of sizes. It is quite realistic to expect the existence of particles of sizes smaller than the resolution limit of the microscope.

Thus, one origin of particles is due to the dispersion of the column packing polymers. This origin gives intrinsically large background scattering that can pose a big challenge to any effort to enhance the signal-to-noise ratio for higher sensitivity protein detection. These debris are also likely responsible for the gradually slowed flow rate as they deposited in the void volume as microscopic "silt" to effectively plug certain paths, leading to gradual net slower flow rate over time.

Figure 9A:
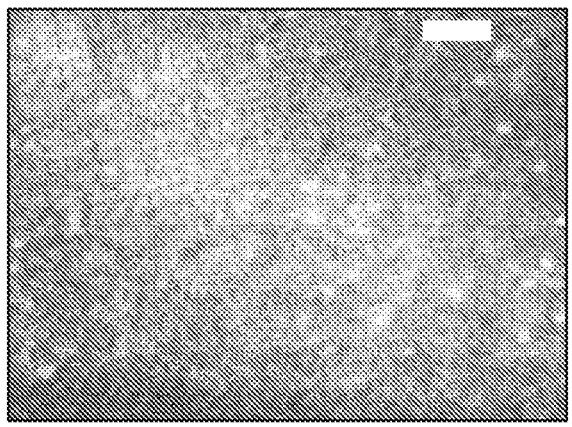
FIGS. 9a-d is a collection of four snapshots on a BSA peak, wherein FIG. 9d was at the peak, FIG. 9c was 64 seconds earlier, FIG. 9b was 89 seconds earlier and FIG. 9a was 3 minutes earlier.
Figure 9B:
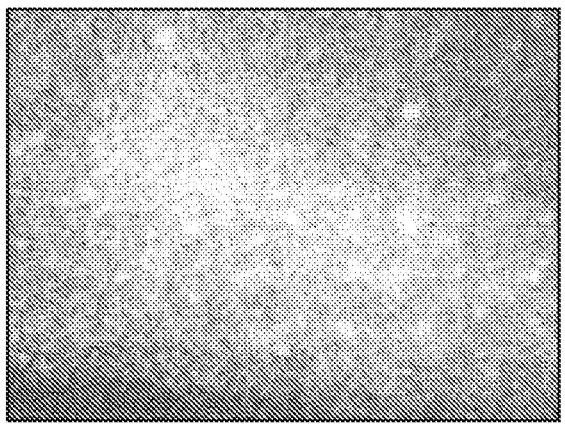
Figure 9C:
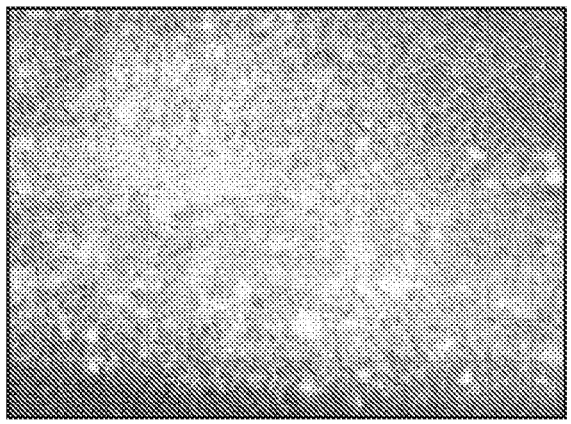
Figure 9D:
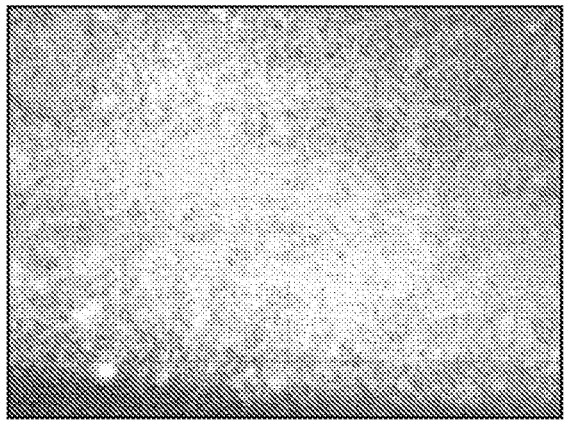

In order to understand the filtration process beyond what can be learned from elution curves, video images were taken as objects emerge from the elution end of the column. FIGS. 9a-d shows a sequence of snapshots collected as a BSA scattering peak was developing. FIG. 9d was at or close to the top of the peak. Images in parts a-c were taken earlier. Note the growing of a uniform bright background over a large region in the middle of the screen without altering much the total number of particles and their sizes. A similar feature was also observed with FITC-labeled proteins. Because the size of either the protein or the FITC molecule is much smaller than the wavelength, the uniform bright background in the image must be due to scattering from individual proteins (or FITC for labeled proteins). Thus, the Rayleigh scattering by individual proteins caused a uniform increase of the background. This phenomenon indicates that those observed scattering centers in pure solutions should be due to particles or aggregates of sizes much larger than that of a protein, originated from the dispersion of the column packing materials.

Optical images taken of the LZ peak showed markedly different structural features from those of the BSA peak. FIGS. 10a-h show snapshot images by the green and red lasers captured on the LZ peak. The image in FIG. 10f was taken at the peak, and images in FIGS. 10a-e were taken earlier with relative time advancement given in the caption.

Figure 10A:
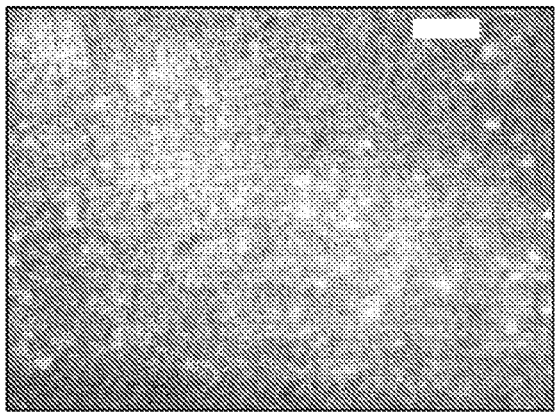
FIGS. 10a-h is a collection of four snapshots by the green laser (FIGS. 10a-d) and two snapshots by the red laser (FIGS. 10e-h) on LZ peaks, with FIG. 10f at the peak, FIG. 10e being at 4 seconds earlier, FIG. 10d being at 8 seconds earlier, FIG. 10c being at 9 seconds earlier, FIG. 10b being at 10 seconds earlier, and with FIG. 10a being at 15 seconds earlier, and also with FIG. 10h at the peak (not too bright due to the smaller power of the red laser) and FIG. 10g being at 14 seconds earlier (the scale bar is 0.1 mm)
Figure 10B:
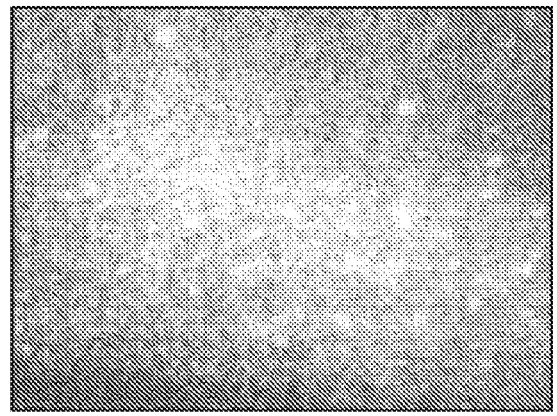
Figure 10C:
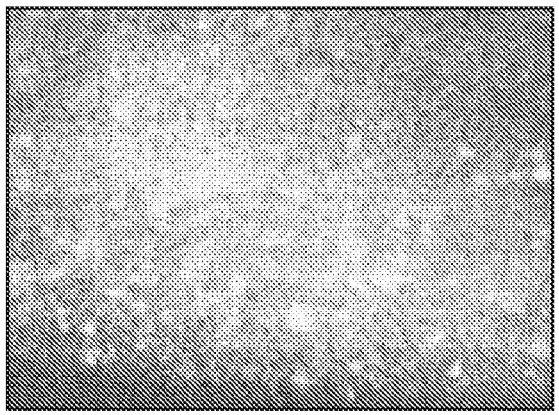
Figure 10D:
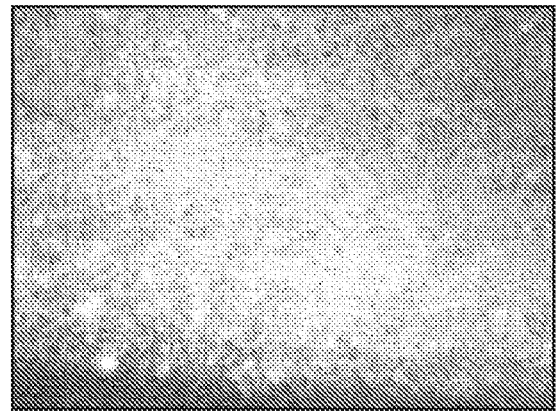
Figure 10E:
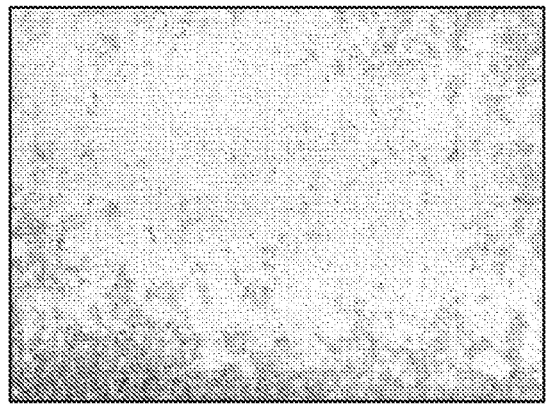
Figure 10F:
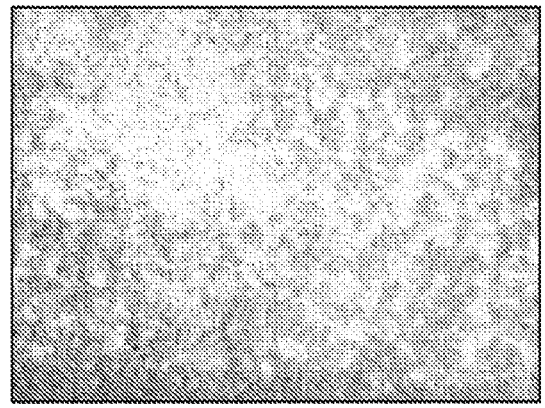
Figure 10G:
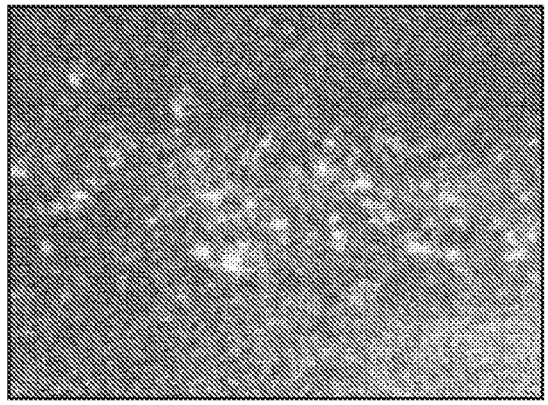
Figure 10H:
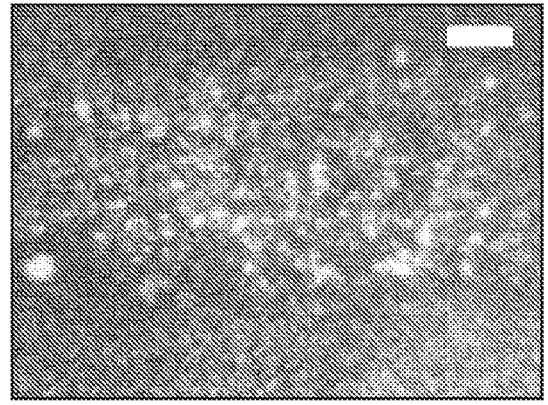

Note that the image in FIG. 10e appears to have the total light illumination similar to or stronger than that in FIG. 10f. This is due to a graphic artifact where the intensity saturation appears on the screen (or the printout) for a number of pixels, although the actual readings for those pixels have not yet reached saturation. Thus, with the instrument, the total illumination is higher in part f than in FIG. 10e. The two images with the red laser were taken at the peak (FIG. 10h) and earlier (FIG. 10g). The main feature is the lack of the uniform bright background in all images. Instead, more and more particles appeared as the LZ peak was developing, and scattering spots became brighter, grew larger, and started to overlap each other.

The appearance of these very bright spots was in sharp contrast of scattering from individual protein or fluorophores. This phenomenon and that a variation of incident angle by 2° caused the disappearing of the LZ scattering peak strongly suggest that the scattering from LZ is due to some kind of coherent scattering. In order to understand this phenomenon, it is important to briefly discuss certain fundamental properties of light and how light interacts with materials.

Characteristics of Light Scattering and Interference

Light detection techniques are especially suitable for biological applications because the probing is noninvasive and under native environments. With the current technology of highly sensitive detectors and lasers, there are great potentials with both direct light scattering and the use of fluorescence tags for gel filtration applications. In principle, because of the capability to detect a single fluorophore, it is possible to detect tiny amounts of eluted proteins. However, the dispersion of polymeric packing materials could be problematic. Therefore, for future developments, the first priority is to reduce or eliminate debris to allow the use of the full potential of high-sensitivity light detection.

It is well-known that for a linearly polarized incident light of intensity $I_0$, the Rayleigh scattering is essentially the dipolar radiation with the dipole moment along the polarization direction. The scattering intensity has an angular distribution function of the form $$I(\theta) = I_0 9\pi^2 \left(\frac{V^2}{\lambda_1^4}\right)\left(\frac{\varepsilon_2 - \varepsilon_1}{\varepsilon_2 + 2\varepsilon_1}\right)^2 \sin^2\theta \quad (2)$$

where $\theta$ is the angle measured from the polarization direction, V is the volume of the scattering body, $\lambda_1$ is the wavelength of the incident beam in the medium (the running buffer), $\varepsilon_1$ is the dielectric constant of the medium, and $\varepsilon_2$ is the dielectric constant of the scattering body. Thus, according to the property of the sine function, it is natural that the orthogonal scattering intensity is at the maximum with the polarization axis horizontal because then the angle $\theta$ is 90°. Similarly, the scattering intensity should be at the minimum when $\theta$ is 0° (or 180°), corresponding to vertical polarization in the experimental setup.

In addition to detecting the scattering intensity, the microscope also allows direct imaging to elucidate microscopic structures of eluted materials. Surprisingly, the structural information is especially useful, such as revealing the presence of debris in the column packing materials, so it helps to prioritize directions for future improvements. Most importantly, structural studies unambiguously reveal a major distinction in scattering characteristics by LZ from BSA, far more than a simple difference in net scattering intensities.

According to scattering intensities alone, it was possible to attribute the larger scattering amplitude by LZ to the higher concentration. Of course, then this scenario is not consistent with the disappearance of the LZ peak by a small variation of the incident angle.

Eluted structures reveal how markedly different BSA and LZ scattered light. The scattering of LZ is similar to that of much larger particles, while the scattering by BSA gives rise to a uniform illumination, consistent with the fact that scattering bodies are much smaller than the wavelength of the incident beam. However, LZ does elute at a much later time than BSA, consistent with its smaller molecular weight. Thus, LZ moves in the column as expected for its smaller molecular weight but scatters the light as a much larger particle. Moreover, the scattering by LZ can be almost nondetectable in cases with just a small variation of the incident angle.

In order for smaller proteins to scatter light as much larger particles, the scattered light must be somehow coherent so the light collected by the microscope is due to constructive interference. The other alternative would be due to instantaneously induced aggregates under specific experimental conditions. The only specificity in this study was the laser irradiation. Then, any aggregation would have been laser induced. However, the conjecture of any laser-induced aggregation became baseless with the disappearance of the LZ peak by the variation of the incident angle while the transmitted beam was still of the same power.

Figure 11:
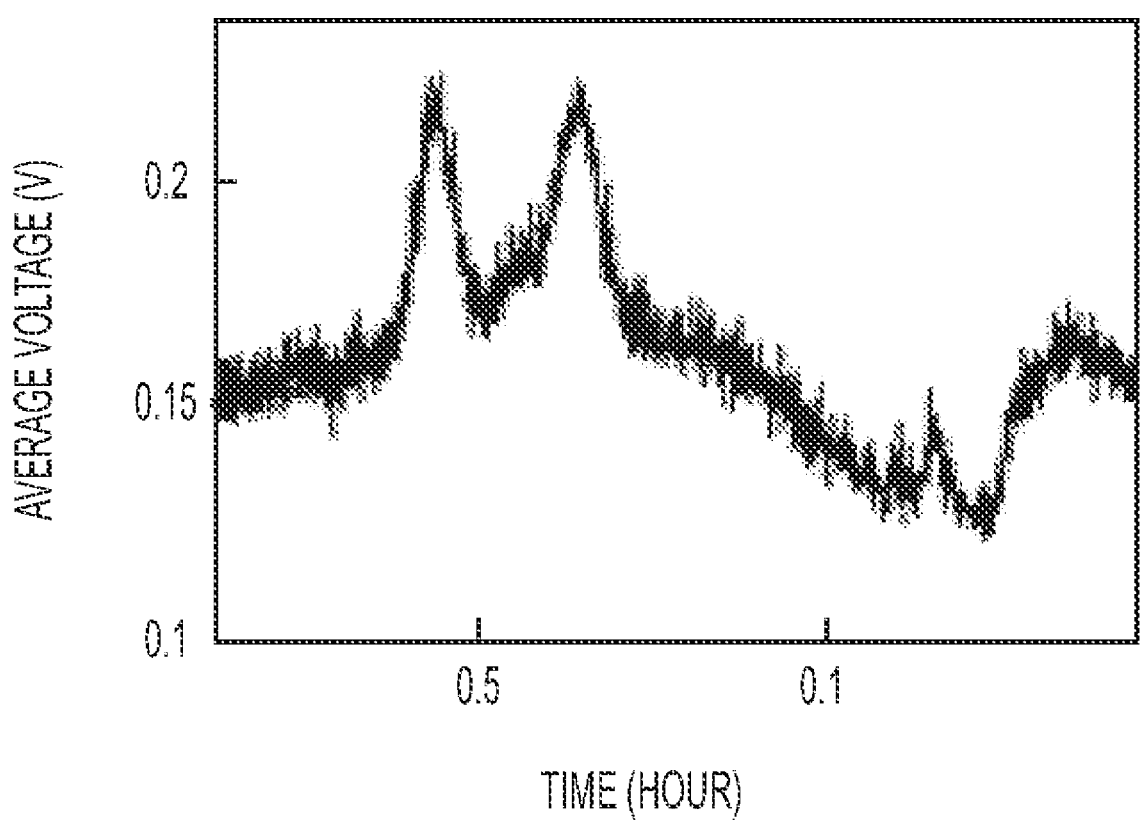
FIG. 11 is a graph of average voltage versus time showing an elution profile for a sample containing BSA and LZ (not prepared in the same batch as the samples of FIGS. 5a and 6a-b) obtained using a 5 mW red laser, wherein the dip corresponds to the elution of LZ.

Actually, numerous runs were attempted, revealing the characteristic two kinds of features as the two curves shown in FIG. 6b. There were also elution patterns where the LZ peak became a dip when the background scattering was very high. FIG. 11 shows an example where the dip corresponded to the elution of LZ. Here the background was very high and irregular due to an unusual large number of debris. The reason for such unusual background was not clear, and this was not the only time that happened. However, the two elution peaks and an elution dip were clearly shown riding on the irregular background. Particularly, the large background made it easy to bring out the feature of the dip that initially tended to go up and then turned down to result in a smooth well as LZ eluted.

According to experimental results it is certain that the scattering from LZ is actually cooperative and coherent and that from BSA and BD2000 is simply the Rayleigh scattering. Thus, coherent scattering is certainly protein-dependent. It may also depend on the secondary structures of proteins. Detailed investigation of the coherent phenomenon and the underlying physical mechanisms are beyond the scope of the present report, and thorough studies from various aspects are required to understand the nature of this phenomenon.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for performing at least one of gel filtration, liquid chromatography and particle purification, comprising:
    a liquid system containing a packing material and receiving a mixture containing particles during use, said fluid system defining a flow path for facilitating smooth flow of the mixture;
    a light source configured and located to illuminate a portion of said flow path with coherent light in a direction along said flow path so as to cause light scattering by ones of the particles in the mixture; and
    an optical sensor for detecting the light scattering;
    wherein;
        said light source is located external to said flow path and said liquid system includes a multitask tube that includes a directional bend that allows said light source to illuminate said portion of said flow path in said direction; and
        said multitask tube includes an effluent section immediately adjacent said directional bend, said effluent portion containing said portion of said flow path, said multitask tube having a flat face opposite said effluent section and perpendicular thereto for receiving light from said light source.

2. A system according to claim 1, wherein said fluid system comprises a filtration column, and the light scattering occurs downstream of said filtration column.

3. A system according to claim 1, further comprising an optical magnification system located between said portion of said flow path and said optical sensor; said optical magnification system configured to magnify a focal plane within the portion of said flow path illuminated by said illuminator.

4. A system according to claim 3, wherein said optical magnification system includes an optical microscope that includes an objective lens.

5. A system according to claim 4, wherein said portion of said flow path is located in a guiding tube, the liquid chromatography system further including an optical cell located proximate said objective lens and surrounding said portion of said flow path outside of said guiding tube.

6. A system according to claim 1, wherein said optical sensor includes a CCD sensor.

7. A system according to claim 1, wherein said optical sensor has an output, the liquid chromatography system further comprising a video signal amplitude detector operatively coupled to said output of said optical sensor.

8. A system according to claim 1, wherein said fluid system includes a filtration column for receiving the packing material, said filtration column having an inside diameter no greater than 5 mm.

9. A system according to claim 8, wherein said filtration column has an inside diameter no greater than 2 mm.

10. A system according to claim 9, further comprising a fluid pump for pumping the solution through said filtration column.

11. A system according to claim 1, wherein said multitask tube has a substantially right-angle bend.

12. A system according to claim 1, wherein said multitask tube is cylindrical and said directional bend is submerged in a refractive index compensation medium that receives light from said light source during use.

13. A system according to claim 1, wherein said effluent section includes a cone tip having an opening, said cone tip configured so as to block light in said effluent section from exiting said cone tip except through said opening.

14. A system according to claim 1, wherein said light source comprises at least one laser.

15. A system according to claim 1, further comprising a plurality of light sources arranged to promote interference patterns in the light scattering.

16. A liquid chromatographic system, comprising:
    a filtration column containing a packing material;
    a fluid delivery system for providing a transport liquid to said filtration column under pressure;
    a guiding tube located downstream from said filtration column, said guiding tube having a flow axis;
    a light source for providing coherent light beam;
    a light transmission unit fluidly coupled between said filtration column and said guiding tube, said light transmission unit for transmitting the coherent light beam along said flow axis of said guiding tube so that when a mixture of particles and the transport liquid is flowing through said guiding tube the particles cause scattering of the coherent light beam; and an imaging system for obtaining image signals of the scattering;

wherein:

said light transmission unit includes a multitask tube fluidly coupled between said filtration column and said guiding tube, said multitask tube including:
a directional bend;
an effluent section immediately adjacent said directional bend; and
a flat face opposite said effluent section and perpendicular thereto for receiving light from said light source; and
said light source is located external to said multitask tube, and said directional bend is provided for directing the coherent light beam along said flow axis of said guiding tube.

17. A liquid chromatographic system according to claim 16, further comprising an optical magnification system optically located between said imaging system and said guiding tube for magnifying a focal plane within said guiding tube.

18. A liquid chromatographic system according to claim 16, wherein said filtration column comprises a capillary tube containing said packing material.

19. A method of performing at least one of particle detection, particle identification and particle characterization, comprising:
flowing a liquid mixture containing particles through a packing material so as to produce an effluent from the packing material;
flowing the effluent through a guiding tube having a flow axis;
flowing the effluent through a multitask tube having:
a directional bend;
an effluent section immediately adjacent said directional bend and in fluid communication with the guiding tube; and
a flat face opposite said effluent section and perpendicular thereto;
illuminating at least a portion of the effluent in the guiding tube with light from outside the multitask tube and shone through the flat face of the multitask tube;
sensing a portion of the light scattered by ones of the particles in the guiding tube so as to provide light-scattering data; and
collecting the light-scattering data over a period of time.

20. A method according to claim 19, wherein said flowing of the solution through the packing material includes flowing the liquid mixture through a tube having an inside diameter no greater than 2 mm, the tube containing the packing material.

21. A method according to claim 20, wherein said flowing of the liquid mixture through the packing material includes pumping the liquid mixture through the tube.

22. A method according to claim 19, wherein said illuminating of the at least a portion of the effluent includes illuminating the at least a portion of the effluent with at least one laser beam.

23. A method according to claim 22, wherein said illuminating of the at least a portion of the effluent includes illuminating the at least a portion of the effluent with a plurality of laser beams so as to promote interference in the light scattered by ones of the particles in the guiding tube.

24. A method according to claim 19, further comprising, prior to said sensing of the portion of the light scattered by the ones of the particles, magnifying the ones of the particles in the guiding tube.

25. A method according to claim 19, wherein said sensing of the portion of the light scattered by the ones of the particles includes generating a video signal.

26. A method according to claim 25, further comprising averaging the video signal so as to obtain an average-intensity signal.

27. A method according to claim 26, further comprising plotting the average-intensity signal versus time.

* * * * *